(12) United States Patent
Krauss et al.

(10) Patent No.: US 8,456,151 B2
(45) Date of Patent: Jun. 4, 2013

(54) MEASUREMENT SENSOR, METHOD FOR ANALYZING A NONPOLAR LIQUID, METHOD FOR MANUFACTURING A MEASUREMENT SENSOR

(75) Inventors: Andreas Krauss, Tuebingen (DE); Gottfried Flik, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 740 days.

(21) Appl. No.: 12/547,836

(22) Filed: Aug. 26, 2009

(65) Prior Publication Data

US 2010/0060260 A1 Mar. 11, 2010

(30) Foreign Application Priority Data

Sep. 10, 2008 (DE) .......................... 10 2008 041 960

(51) Int. Cl.
*G01R 27/22* (2006.01)

(52) U.S. Cl.
USPC ............................................................. 324/92

(58) Field of Classification Search
None
See application file for complete search history.

(56) References Cited

U.S. PATENT DOCUMENTS

| | | | | |
|---|---|---|---|---|
| 4,486,292 A | * | 12/1984 | Blackburn | 257/410 |
| 4,882,292 A | * | 11/1989 | Sudholter et al. | 438/49 |
| 5,077,229 A | * | 12/1991 | Forlani | 438/49 |
| 7,649,358 B2 | * | 1/2010 | Toumazou et al. | 324/438 |

* cited by examiner

*Primary Examiner* — Jermele M Hollington
(74) *Attorney, Agent, or Firm* — Kenyon & Kenyon LLP

(57) ABSTRACT

A measurement sensor for analyzing a nonpolar liquid contains a field effect transistor that has an exposed gate contact for wetting with the nonpolar liquid, and an electrical shield that surrounds the gate contact and has openings for inflow and outflow of the nonpolar liquid.

9 Claims, 1 Drawing Sheet

MEASUREMENT SENSOR, METHOD FOR ANALYZING A NONPOLAR LIQUID, METHOD FOR MANUFACTURING A MEASUREMENT SENSOR

BACKGROUND INFORMATION

U.S. Pat. No. 4,882,292 describes a ChemFET for the analysis of polar liquids.

SUMMARY OF THE INVENTION

One aspect of the present invention relates to a measurement sensor for analyzing a nonpolar liquid, having a field effect transistor that has an exposed gate contact for wetting with the nonpolar liquid, and an electrical shield that surrounds the gate contact and has openings for inflow and outflow of the nonpolar liquid.

In nonpolar liquids, the use of a reference electrode in the conventional sense is not advisable, since no electrical or even ionic currents flow in order to compensate for potential differences in the liquid. A reference potential is introduced according to the present invention by the fact that the entire environment of the ChemFET is brought to a defined potential by means of the electrical shield.

A further aspect relates to a method for analyzing a nonpolar liquid by sensing the conductivity of a current channel of a field effect transistor whose gate dielectric is wetted by the nonpolar liquid.

A further aspect relates to a method for manufacturing a measurement sensor, having the steps of: patterning drain and source regions in a semiconductor substrate, depositing a gate dielectric above a gate channel defined by the drain and source regions, making contact to the drain and source regions, burying the gate dielectric in a sacrificial material, depositing a conductive semiconductor layer on the sacrificial material above the gate dielectric, introducing openings into the conductive semiconductor layer in order to form the electrical shield, and under-etching the conductive semiconductor layer in order to expose the gate dielectric.

DETAILED DESCRIPTION

Figure 1:
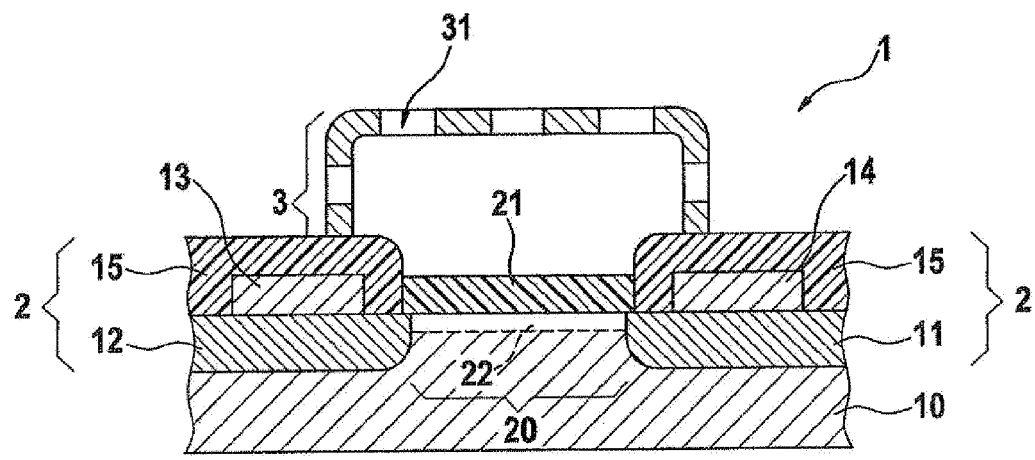
FIG. 1 is a partial cross section of a measurement sensor.
Figure 2:
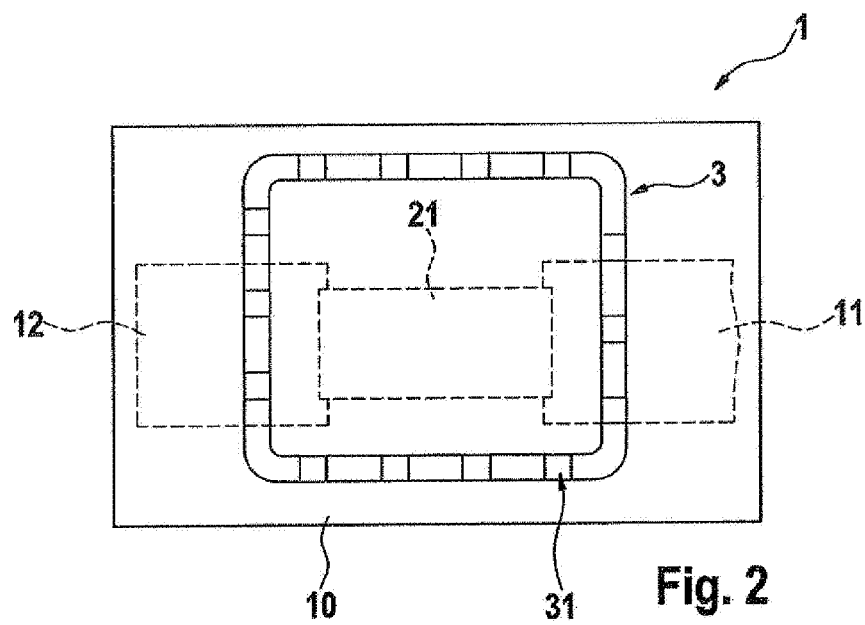
FIG. 2 is a plan view of the measurement sensor of FIG. 1.

An embodiment of a measurement sensor 1 will be explained with reference to a partial cross section in FIG. 1. FIG. 2 shows measurement sensor 1 in a plan view. Measurement sensor 1 has a ChemFET 2 and an electrical shield 3.

ChemFET 2 is patterned into a semiconductor substrate 10. Semiconductor substrate 10 is doped with a dopant of a first conductivity type. Two regions for source 11 and drain 12, doped with a dopant of a second conductivity type, are introduced into semiconductor substrate 10. Source 11 and drain 12 are contacted via electrodes 13, 14. Source 11, drain 12, and electrodes 13, 14 are encapsulated by an insulating protective layer 15.

A gate dielectric 21 is applied above a channel region 20 between source 11 and drain 12. Gate dielectric 21 influences the conductivity of a gate channel 22 that can form in substrate 10 adjacently to gate dielectric 21 and between source 11 and drain 12.

Gate dielectric 21 can be grown or deposited onto semiconductor substrate 10.

Examples of gate dielectric 21 encompass $Al_2O_3$, $Si_3N_4$, $SiO_2$, diamond, polycrystalline or amorphous SiC, and polymers having a high chemical resistance to fuels (e.g. stabilized polyamides, polyether ether ketone, polyether sulfone, polyphenylene sulfide, partly or entirely halogenated or fluorinated olefins), and layer combinations thereof. The gate dielectric can furthermore be additionally coated with swellable plastics or porous materials. In the embodiment depicted, gate dielectric 21 is not covered with a further layer, but is exposed and can be brought into contact with a liquid.

Gate dielectric 21 is at a floating potential, since it is not coupled via an electrode to a reference potential. Gate dielectric 21 assumes the potential of the environment. The electric fields at gate dielectric 21 are thus defined by the environment.

The nonpolar liquid, and substances dissolved or emulsified in the nonpolar liquid, adsorb at the exposed surface of gate dielectric 21. There is a characteristic adsorption rate for each combination of a substance and the material selected for gate dielectric 21. Adsorption results in modified electrostatic fields, and influences the dielectric properties of gate dielectric 21. The change in gate dielectric 21 has an effect on the conductivity of gate channel 22, which conductivity can be evaluated by an external circuit (not described here). The evaluation can be supported by tables from which the nature and quantity of the substances can be ascertained based on an absolute change in conductivity, a rate of the change in conductivity, etc.

An electrical shield 3 is arranged on protective layer 15. Electrical shield 3 surrounds gate dielectric 21. A constant electrical potential that is predefined by the potential of electrical shield 3 exists inside electrical shield 3. The nonpolar liquid, like a vacuum, exerts no influence on the electrical fields and potentials inside the shield. Electrical shield 3 can be set to a defined electrical potential.

Electrical shield 3 can be constituted from doped semiconductor material or from a metal, in particular of the platinum group or gold.

Electrical shield 3 has openings 31 through which the nonpolar liquid can flow through electrical shield 3. Openings 31 can be introduced into electrical shield 3 by way of an etching method.

A method for manufacturing measurement sensor 1 can make use of the following steps: Firstly a FET having a source 11, drain 12, a gate channel 22, and a gate dielectric 21 is produced. The method steps necessary for this are sufficiently known and will therefore not be discussed further.

A sacrificial material is applied locally onto gate dielectric 21. The sacrificial material is selected from materials that can be selectively etched with respect to the gate dielectric. A layer of conductive semiconductor material is deposited on the sacrificial material. The layer can be supported mechanically on an insulating layer above source 11 and drain 12. The conductive semiconductor material can encompass, for example, porous silicon carbide. Openings 31 can be formed through the pores of the porous silicon carbide. With other conductive semiconductor materials, openings 31 can be etched into the layer in the vicinity of gate dielectric 21 using masking steps. The layer, patterned in this fashion, forms electrical shield 3. The sacrificial material is removed selectively with respect to electrical shield 3 and gate dielectric 21, or can remain as a porous protective layer on the gate at an unmodified or reduced layer thickness.

Gate dielectric 21 can be coated with a thin metal layer, e.g. 1 nm to 3 nm, for example gold or a platinum metal. The interface of the metal with gate dielectric 21 influences the conductivity of gate channel 22. The interface, and consequently also the conductivity of gate channel 22, are influenced in the context of adsorption onto the thin metal layer. Adsorption rates onto the metal layers differ from those onto dielectric materials, as does their influence on gate channel 22.

Measurement sensor 1 can have two or more ChemFETs whose gate dielectrics 21 have different material compositions or are coated with other metals. The different correlations with the adsorbed substances allow their quantities to be sensed separately from one another.

Gate dielectric 21 can have a swelling polymer. In particular, a polymer that swells in gasoline, diesel fuel, kerosene, or oil can be used.

Electrical shield 3 surrounding the field effect transistor can be set to a varying, e.g. oscillating, electrical potential. Functional monitoring of the sensor can be carried out by way of the variation in potential. Further information regarding the analytes, e.g. dielectric properties, can likewise be determined by way of a varying potential.

What is claimed is:

1. A measurement sensor for analyzing a nonpolar and nonconductive liquid, comprising:
    a field effect transistor having an exposed gate contact configured to be wetted by the liquid; and
    an electrical shield surrounding the gate contact and having openings for inflow and outflow of the liquid, the electrical shield configured to set an electrical potential of an environment of the gate contact.

2. The measurement sensor according to claim 1, wherein the exposed gate contact has an exposed gate dielectric.

3. The measurement sensor according to claim 1, wherein the exposed gate contact is at a floating electrical potential.

4. The measurement sensor according to claim 1, wherein the electrical shield is manufactured from a semiconductor material.

5. The measurement sensor according to claim 1, wherein the electrical shield and the field effect transistor are integrated on one chip.

6. A method for analyzing a nonpolar and nonconductive liquid, the method comprising:
    sensing a conductivity of a current channel of a field effect transistor whose gate dielectric is wetted by the liquid; and
    setting an electrical potential of an environment of the gate dielectric by an electrical shield surrounding the gate dielectric.

7. The method according to claim 6, further comprising bringing the electrical shield surrounding the gate dielectric to a constant electrical potential.

8. The method according to claim 6, further comprising bringing the electrical shield surrounding the gate dielectric to a varying electrical potential.

9. The method according to claim 6, further comprising applying a polymer coating that exhibits entirely or partly selective uptake of constituents of the liquid between the gate dielectric and liquid.

* * * * *